(12) United States Patent
Thompson et al.

(10) Patent No.: US 8,507,285 B2
(45) Date of Patent: Aug. 13, 2013

(54) METHODS AND DEVICES FOR IDENTIFYING BIOPOLYMERS USING MASS SPECTROSCOPY

(75) Inventors: Dean R. Thompson, Fort Collins, CO (US); Steven M. Fischer, Hayward, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 2329 days.

(21) Appl. No.: 10/388,088

(22) Filed: Mar. 13, 2003

(65) Prior Publication Data

US 2004/0180446 A1    Sep. 16, 2004

(51) Int. Cl.
*G01N 33/00*    (2006.01)
(52) U.S. Cl.
USPC .............. 436/86; 436/89; 436/94; 436/173; 435/6.1; 435/7.4; 702/19
(58) Field of Classification Search
None
See application file for complete search history.

(56) References Cited

U.S. PATENT DOCUMENTS

| | | | |
|---|---|---|---|
| 5,470,753 A | 11/1995 | Sepetov et al. | |
| 5,538,897 A * | 7/1996 | Yates et al. | 436/89 |
| 5,936,241 A | 8/1999 | Franzen et al. | |
| 6,017,693 A | 1/2000 | Yates, III et al. | |
| 6,051,378 A | 4/2000 | Monforte et al. | |
| 6,104,027 A | 8/2000 | Gee et al. | |
| 6,271,037 B1 | 8/2001 | Chait et al. | |
| 7,351,957 B2 * | 4/2008 | Bloomfield et al. | 250/282 |
| 2003/0068825 A1 * | 4/2003 | Washburn et al. | 702/19 |

FOREIGN PATENT DOCUMENTS

| | | | |
|---|---|---|---|
| WO | WO 94/16101 | * | 7/1994 |
| WO | WO 02/061047 A2 | | 8/2002 |
| WO | WO 03/000931 A1 | | 1/2003 |

OTHER PUBLICATIONS

Krane et al. "Fundamental Concepts of Bioinformatics", 2003 Person Education, Inc., pp. 42-45.*
Lennon "Matrix Assisted Laser Desorption Ionization Time-of-flight Mass Spectrometry", ABRFNews, Jun. 1997 http://www.abrf.org/ABRFNews/1997/June1997/jun97lennon.html.*
Mørtz et al. "Sequence tag identification of intact proteins by matching tandem mass spectral data against sequence data bases", Proc. Natl. Acad. Sci. USA, Aug. 1996, v. 93, pp. 8264-8267.*
Thorne et al. "Elucidation of Some Fragmentations of Small Peptides Using Sequential Mass Spectrometry on a Hybrid Instrument", Rapid Commun. Mass Spectrom, 1989, v. 3. No. 7.*
Ashcroft "An Introduction to Mass Spectrometry", 2006, http://www.astbury.leeds.ac.uk/facil/MStut/mstutorial.htm.*
Dell et al. "Glycoprotein Structure Determination by Mass Spectrometry", Science, 2001, v. 291, pp. 2351-2356.*
Burks et al. Methods in Enzymology, vol. 183, 1990, pp. 3-22.*

(Continued)

*Primary Examiner* — Sally Merkling

(57) ABSTRACT

A method of identifying a biopolymer in a sample that includes one or more biopolymers. The biopolymers may be polypeptides, polynucleotides, or polysaccharides. The method makes use of mass spectral datasets. A first dataset includes measured masses of the one or more biopolymers that are in the sample. A second dataset includes measured masses of a collection of fragments of the one or more biopolymers. The method selects a mass from the first dataset and then matches masses from the second dataset with the selected mass. The matched masses represent fragments of the biopolymer with the selected mass. Once the masses in the second dataset have been matched they are compared to determine a monomer sequence for the biopolymer with the selected mass. The method may be repeated with additional masses in the first dataset.

64 Claims, 2 Drawing Sheets

(56) References Cited

OTHER PUBLICATIONS

Masselon, et al. "Accurate Mass Multipexed Tandem Mass Spectrometry for High-Throughput Polypeptide Identification from Mixtures," Analytical Chemistry,72:1918-1924, Apr. 2000.

Goodlett, et al. "Protein Identification with a Single Accurate Mass of a Cysteine-Containing Peptide and Constrained Database Searching," Analytical Chemistry, 72:1112-1118, Mar. 2000.

Horn, et al. "Automated de novo Sequencing of Proteins by Tandem High-Resolution Mass Spectrometry," PNAS, 97(19):10313-10317, Sep. 2000.

Li, et al. "High-Throughput Peptide Identification from Protein Digests Using Data-Dependent Multiplexed Tandem FTICR Mass Spectrometry Coupled with Capillary Liquid Chromatography," Analytical Chemistry, 73:3312-3322, Jul. 2001.

European Search Report Dated: Aug. 9, 2004.

* cited by examiner

METHODS AND DEVICES FOR IDENTIFYING BIOPOLYMERS USING MASS SPECTROSCOPY

BACKGROUND OF THE INVENTION

Mass spectroscopy (MS) has emerged as a powerful analytical tool for studying biopolymers, e.g., polypeptides, polynucleotides, and polysaccharides due to its high sensitivity, speed, and capability for analysis of highly complex mixtures. For example, a variety of techniques have been developed for identifying proteins in biological samples (e.g., cell extracts). Typically, the proteins in a sample of interest are first separated by two-dimensional gel electrophoresis (2D Gel). Selected gel spots are then excised and digested with one or more digestive enzymes (e.g., trypsin) to break the proteins into collections of shorter polypeptide chains. These digests are then analyzed via mass spectroscopy and the resulting spectra are compared to spectra predicted from amino acid sequence information contained in databases (e.g., SwissProt/TrEMBL, NCBI Protein Database, etc.). Identifications are made based on the improbability of more than one protein matching the observed spectra (e.g., see Strupat et al., *Anal. Chem.* 66:464, 1994). A basic limitation of polypeptide mass fingerprinting, as this approach is commonly called, stems from the fact that it can only be used to identify proteins for which sequences are already known; it is incapable of identifying previously unknown proteins.

In general, 2D Gel separations have proven to be slow and time consuming, thus higher throughput methods using multi-dimensional liquid chromatography (MDLC) have also been developed (e.g., see Yates et al., *Anal. Chem.* 69:767, 1997). Several variations of this process are in use, but they all typically begin with an enzymatic digestion of the proteins present in the sample, resulting in a complex mixture containing polypeptide chains from many different proteins. This complex mixture is then separated via MDLC, typically using Strong Cation Exchange (SCX) followed by Reverse Phase (RP). The resulting separations typically contain polypeptides from multiple proteins. These separations are analyzed via mass spectroscopy and the results compared to predicted spectra as before. In most cases, tandem mass spectroscopy (MS/MS) is used to perform the analysis (e.g., see Ducret et al., *Protein Sci.* 7:706, 1998). In this process, polypeptides eluting from the separation stage are analyzed in the first stage of a tandem mass spectrometer that selects certain polypeptide ions for fragmentation and analysis in the second stage of the tandem mass spectrometer. The resulting spectra give more detailed information about the structure of the selected polypeptide ions, improving the identification.

One of the problems with the use of MDLC and MS/MS for protein identification is that it is difficult to get broad coverage of the proteins present in a sample. This can usually be attributed to the process used to select ions in the first stage for fragmentation in the second stage. Good identification can be made if a sufficient number of polypeptides from a given protein are selected for fragmentation. However, since the process of selecting polypeptides and collecting spectra in the second stage is slow relative to flow from the separation stage, it is not always possible to select all polypeptides present in an elution peak for analysis in the second stage. Algorithms used for selection make real-time decisions based on a variety of factors including relative abundance of an ion in the first stage spectra, and the time since a given mass has been selected. They may also have provisions for providing preference to specific masses or to exclude given masses, but these lists are generally manually constructed. The consequence of these selection approaches is that polypeptides with relatively high levels of abundance (i.e., polypeptides from relatively abundant proteins or common polypeptides that result from the digestion of several different proteins) are preferentially selected. Conversely, polypeptides resulting from proteins with relatively low levels of abundance or less than ideal ionization characteristics are frequently missed.

Tandem mass spectroscopy has an additional problem in that it is difficult to accurately measure the relative amounts of different polypeptides present in a given sample due to the high levels of ion loss associated with the ion selection process. In a complex spectrum where almost all ions are of interest, it is not possible to continuously monitor all the ions and perform MS/MS on each important ion. Since the ion intensity for each ion changes with the chromatographic elution profile of the polypeptide from which the ion is derived, the time spent selecting ions and performing MS/MS greatly reduces the number of data points collected for each ion thereby reducing the accuracy of the estimated amount of each polypeptide present in the sample.

In general, the limitations that are described above with reference to polypeptides also apply when mass spectroscopy is used to identify other biopolymers including polynucleotides and polysaccharides.

SUMMARY OF THE INVENTION

Described herein is a method of identifying a biopolymer in a sample that includes one or more biopolymers. The biopolymers may be polypeptides, polynucleotides, or polysaccharides. The method makes use of mass spectral dataset. A first dataset includes measured masses of the one or more biopolymers that are in the sample. A second dataset includes measured masses of a collection of fragments of the one or more biopolymers. The method selects a mass from the first dataset and then matches masses from the second dataset with the selected mass. The matched masses represent fragments of the biopolymer with the selected mass. Once the masses in the second dataset have been matched they are compared to determine a monomer sequence for the biopolymer with the selected mass. The method may be repeated with additional masses in the first dataset.

BRIEF DESCRIPTION OF THE DRAWING

Features of the present invention will become more apparent from the following detailed description of certain exemplary embodiments thereof taken in conjunction with the accompanying drawing in which.

DESCRIPTION OF CERTAIN EXEMPLARY EMBODIMENTS OF THE INVENTION

Figure 1:
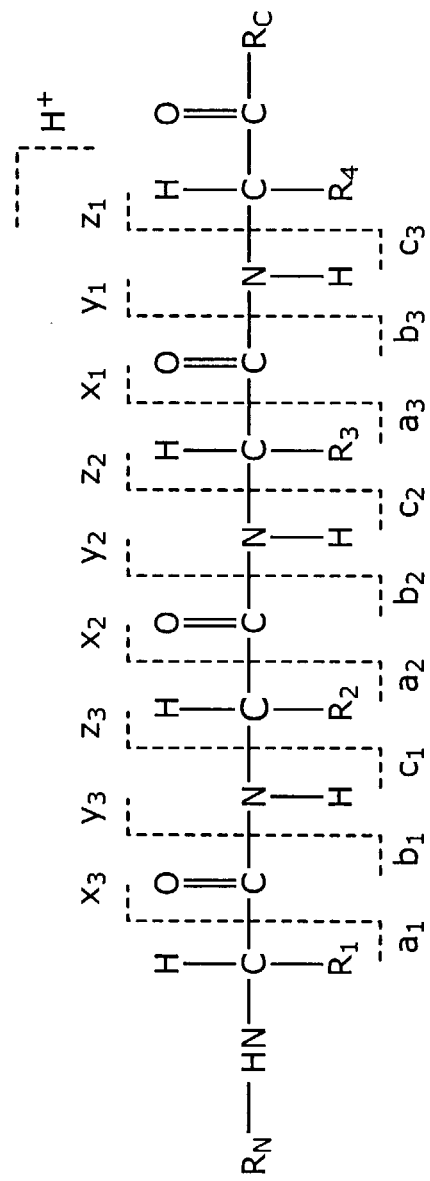
FIG. 1 illustrates the single backbone cleavage events that result in the a/x, b/y, and c/z series of N-/C-terminal polypeptide fragments.

This patent application mentions various patents and published references. The contents of each such item are hereby incorporated by reference. For purposes of simplicity and clarity, the following section describes how the inventive methods may be used to identify polypeptides. This emphasis on polypeptides is intended to be non-limiting. In particular, it is to be understood and will be appreciated by one having ordinary skill in the art that the methods described herein may also be used to identify other biopolymers including polynucleotides and polysaccharides. These additional embodiments are discussed in further detail at the end of this application.

Introduction

In certain embodiments, the present invention provides methods and devices for identifying polypeptides in a sample of interest using high mass accuracy mass spectroscopy. The inventive methods and devices may be used in combination with traditional approaches such as polypeptide mass fingerprinting and MS/MS; however, they do not depend on these methods. In particular, the inventive methods and devices may be used to identify polypeptides based on mass spectral data without making a comparison to a database of known protein sequences. Furthermore, the inventive methods and devices may be used to identify polypeptides based on mass spectra obtained with a single-stage mass spectrometer.

In general, the inventive methods involve analyzing ion masses from one or more sets of mass spectra. Each set of spectra includes at least two different spectra of the sample of interest, namely an "unfragmented" or "U" spectrum and a "fragmented" or "F" spectrum.

A U spectrum includes peaks that correspond to some and preferably all of the polypeptides in the sample when these polypeptides are unfragmented. In preferred embodiments, a U spectrum is obtained by detecting the polypeptides in the sample without exposing them to a fragmentation mechanism. It is to be understood that a U spectrum may, in certain embodiments, include peaks that represent fragments of these polypeptides, e.g., fragments that were inadvertently created as a consequence of the mechanism used to ionize and/or detect the polypeptides in the spectrometer.

An F spectrum includes peaks that correspond to a collection of fragments of some and preferably all of the polypeptides in the sample. In preferred embodiments, an F spectrum is obtained by detecting the polypeptides in the sample after these have been exposed to one or more fragmentation mechanisms. It is to be understood that an F spectrum may, in certain embodiments, include peaks that represent unfragmented polypeptides, e.g., polypeptides that survive exposure to the fragmentation mechanism. It will be appreciated that such situations are most likely to occur when the polypeptides are exposed to relatively low fragmentation energies.

Once the U and F spectra have been obtained, the spectral masses (or "masses") are extracted and analyzed using a variety of processing steps that are described in greater detail below. These processing steps take advantage of the structural information that is available in spectral data having a high level of mass accuracy. The results of the analysis are used to identify one, some or all of the polypeptides in the sample of interest. In certain embodiments identifying a polypeptide involves determining the entire amino acid sequence of that polypeptide. In certain other embodiments, partial amino acid sequences and/or a set of alternative sequences are determined. In yet other embodiments, the nature, location and relative levels of various modifications are determined.

In certain preferred embodiments, the spectra are obtained with a single-stage spectrometer. By eliminating the ion selection step that is required in multi-stage spectroscopy, such embodiments provide broader coverage of the polypeptides present in the sample. The use of a single-stage mass spectrometer also increases the throughput of analysis in an MDLC-MS setup. In addition, as a consequence of the low ion losses that are associated with single-stage instruments, the spectra that are obtained according to these embodiments may be used to provide more accurate information on the relative quantity of the polypeptides present in the sample. In certain embodiments, the methods may be used in conjunction with mass tagging reagents to provide highly accurate measurements of changes in the levels of particular polypeptides between two different samples.

The methods described herein may be applied to any sample that includes one or more polypeptides. In certain embodiments the sample includes a plurality of polypeptides. As defined herein, a "polypeptide" comprises a string of at least three amino acid monomers linked together by peptide bonds and terminated by an N-terminal group and a C-terminal group ($R_N$ and $R_C$, respectively in FIG. 1). It is to be understood that the terms "polypeptide", "oligopeptide", "peptide", and "protein" may be used interchangeably, i.e., for the purposes of the present invention the term polypeptide encompasses full length proteins and fragments thereof, e.g., enzymatic or chemical digestion fragments. The polypeptides may contain commonly occurring amino acid monomers (e.g., those listed in Appendix A) and less commonly occurring amino acid monomers (i.e., amino acid monomers that are not commonly found in proteins but that can be incorporated into a polypeptide chain such as, but not limited to, those listed in Appendix B). The polypeptides may include any N-terminal group and any C-terminal group (e.g., but not limited to those listed in Appendix C). Also, one or more of the amino acid monomers in a polypeptide may be modified, e.g., but not limited to a modification listed in Appendix D and E and/or by addition of a mass tag.

In certain embodiments, the methods may be used to analyze samples produced by chemical "digestion" of one or more proteins, e.g., mixtures from N-terminal Edman and/or C-terminal carboxypeptidase cleavages. The methods may also be used to confirm the sequence of one or more polypeptides in a synthetic polypeptide mixture. In yet other embodiments, the inventive methods and devices may be used to analyze different logical fractions of a polypeptide mixture. For example, without limitation, the inventive methods may be used to analyze different excised spots from a 2D Gel protein separation; different collected fractions from a capillary or free-flow electrophoresis separation, a size exclusion chromatography separation, a one- or multi-dimensional LC separation, e.g., in an LC-MS setup; etc.

Obtaining U and F Spectra

The methods described herein are independent of the ionization technique that is used while obtaining the U and F spectra (i.e., any technique that is capable of ionizing polypeptides may be used including, but not limited to, conventional matrix-assisted laser desorption ionization or MALDI, described by Hillenkamp et al., *Anal. Chem.* 63:193A, 1991; atmospheric pressure matrix-assisted laser desorption ionization or AP-MALDI, described by Moyer and Cotter, *Anal. Chem.* 74:468A 2002; electrospray ionization or ESI, described by Fenn et al., *Mass Spectrom. Rev.* 9:37, 1990; etc.).

The invention is also independent of the detection technique that is used (i.e., any technique that is capable of detecting polypeptides may be used including, but not limited to, time-of-flight spectroscopy or TOF, described by Chernushevich et al., *J. Mass Spectrom.* 36:849, 2001; Fourier transform ion cyclotron resonance spectroscopy or FT-ICR, described by Hendrickson and Emmett, *Annu. Rev. Phys. Chem.* 50:517, 1999; ion trap spectroscopy, described by Jonscher and Yates, *Anal. Biochem.* 244:1, 1997; etc.).

The invention is generally independent of the fragmentation technique (or combination of techniques) that is used to produce F spectra (i.e., any technique that is capable of fragmenting polypeptides may be used including, but not limited to, collision-induced dissociation or CID, described by Falick et al., *J Am. Soc. Mass Spectrom.* 4:882, 1993; post-source decay or PSD, described by Spengler, *J Mass Spectrom.* 32:1019, 1997; infrared multiphoton dissociation or IR-MPD, described by Little and McLafferty, *J Am. Soc. Mass Spectrom.* 7:209, 1996; surface induced dissociation or SID, described by Chorush et al., *Anal. Chem.* 67:1042, 1995; electron capture dissociation or ECD, described by Zubarev et al., *Anal. Chem.* 72:563, 2000; etc.).

Figure 2:
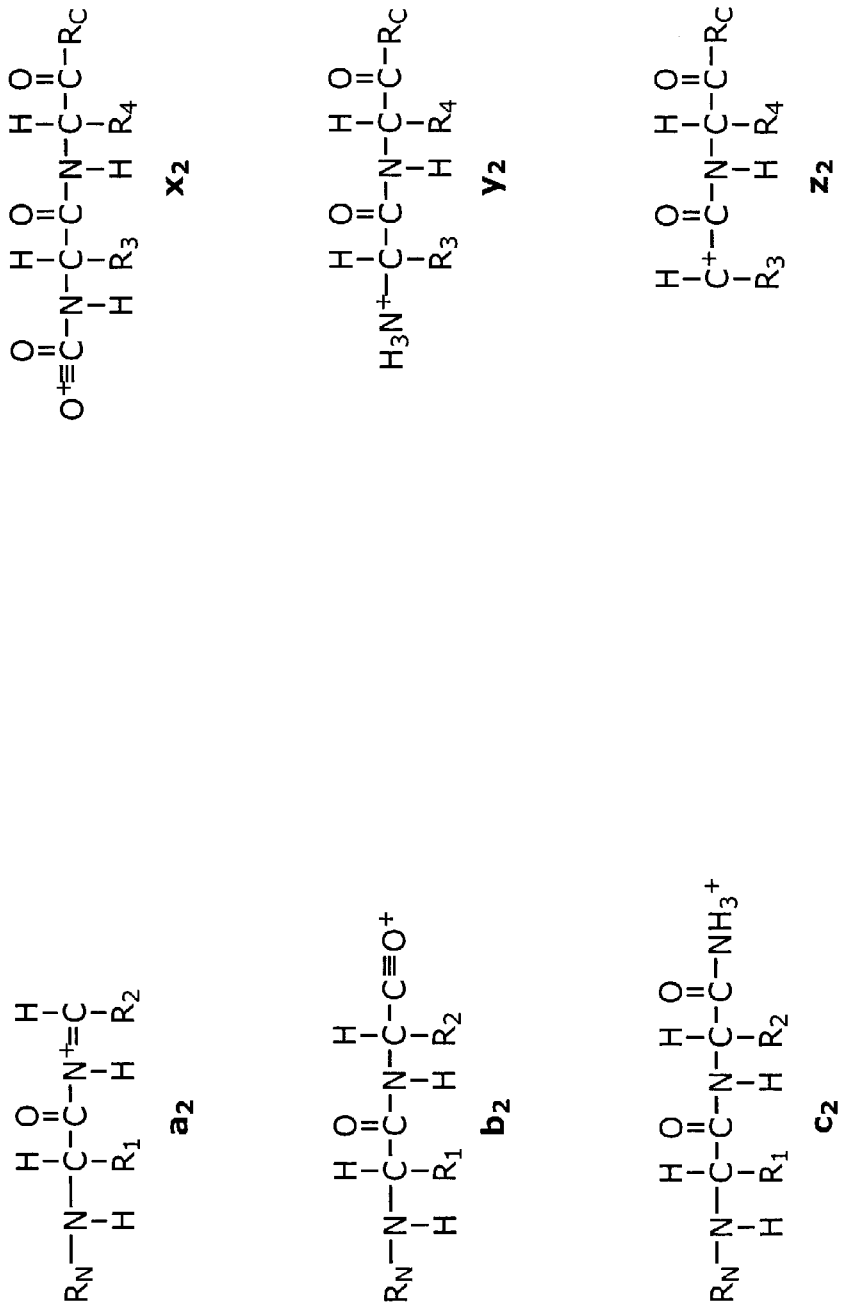
FIG. 2 illustrates the accepted nomenclature for N- and C-terminal fragments produced by the single backbone cleavage events of FIG. 1.

As is well known in the art, the types of F ions in the F spectra will depend on many factors including amino acid sequence, fragmentation method, fragmentation energy, internal energy, charge state, etc. The accepted nomenclature for F ions that result from a single backbone cleavage is depicted in FIGS. 1 and 2 and described in Johnson et al., *Anal. Chem.* 59:2621, 1987. Briefly, N-terminal fragments are classed as either a, b, or c; C-terminal fragments are classed as either x, y, or z; and a subscript indicates the number of monomers in the fragment. As illustrated in FIG. 1, the a/x, b/y, and c/z fragments are produced by cleavage of $C\alpha_i/C_i$, $C_i/N_i$, and $N_i/C\alpha_{i+1}$ backbone bonds, respectively. Typically F spectra may include peaks from more than one F ion of a given type, e.g., one, some or all of a series of a polypeptide with n monomers, i.e., $a_1, a_2, a_3, a_4, a_5, a_6, a_7, a_8, a_9, a_{10}, \ldots, a_{n-2}$, and $a_{n-1}$. In addition F spectra may include different sets of complementary F ions, e.g., one, some or all of the a/x, b/y, and c/z pairs. It will further be appreciated that according to certain embodiments of the invention, F spectra may further include ions that result from a double backbone cleavage, a side chain cleavage, and/or a common neutral loss, e.g., loss of $H_2O$, $NH_3$, etc.

In preferred embodiments, F spectra are generated with a single or combination of low-energy mechanisms. Hashimoto et al. have recently described the combined use of CID and IR-MPD (*Anal. Chem.* Web release on Dec. 24, 2002). It will be appreciated that the exact energy (or energies) used will depend on the sample under analysis and the fragmentation method (or methods) used. In general, appropriate fragmentation energies may be determined empirically, for example, by monitoring the proportion of unfragmented to fragmented peaks as a function of fragmentation energy. Additionally or alternatively one could select suitable fragmentation energies based on the average molecular weight and/or the weight distribution of the detected fragments. In certain embodiments, fragmentation energies may be set at a level below the threshold for double backbone and/or side chain cleavage. For example and without limitation, appropriate fragmentation energies when using CID at relatively high gas pressures will typically be less than about 1000 eV, more typically between about 100 and about 500 eV, even more typically between about 150 and about 250 eV. One having ordinary skill in the art can readily determine appropriate fragmentation energies for other mechanisms such as ECD and SID.

The methods described herein are sensitive to the mass accuracy of the peaks in the U and F spectra. In general, the mass accuracy of the U and F spectra will be affected by the specifications of the mass spectrometer and signal strength. Commercial instrument manufacturers usually specify mass accuracies for their spectrometers in units of parts-per-million (ppm). For example, if the theoretical monoisotopic mass of a known polypeptide is: 1,001.748 Da and the measured monoisotopic mass for that polypeptide is 1,001.752 Da, then the mass accuracy of the spectrometer under those operating conditions is: $(1{,}001.752 - 1{,}001.748)/1{,}001.748 = 4.0 \times 10^{-6}$ or 4.0 ppm.

It is to be understood that the U and F spectra that are analyzed according to the methods described herein may be obtained under a broad range of operating conditions. The accuracy and completeness of the analysis will naturally improve as the mass accuracy is increased. The mass accuracy that is required may depend on the nature of the sample of interest and on the nature of the polypeptides within the sample, e.g., the average molecular weight and/or the range of molecular weights of the polypeptides. In addition, the choice of mass accuracy will depend on the desired quality of the analysis. Without limitation, the spectrometer or spectrometers that are used to obtain the U and F spectra may, for example, be operated under conditions that provide spectra with a mass accuracy of at least about 20 ppm, more preferably between about 10 and about 0.05 ppm, and even more preferably between about 3 and about 0.5 ppm.

Those of ordinary skill in the art will readily recognize that a variety of methods and devices have been described and developed in the art that enable spectra of polypeptides to be obtained with mass accuracies in these preferred ranges, e.g., without limitation those described by Smith et al., *Electrophoresis* 22:1652, 2001; Park and Russell, *Anal. Chem.* 73:2558, 2001; Flora et al., *Anal. Chem.* 73:1247, 2001; Hannis and Muddiman, *J Am. Soc. Mass. Spectrom.* 11:876, 2000; Jiang and Moini, *Anal. Chem.* 72:20, 2000; Green et al., *Anal. Biochem.* 275:39, 1999; Bruce et al., *Anal. Chem.* 71:2595, 1999; Lorenz et al., *Rapid Commun. Mass Spectrom.* 13:2098, 1999; Shi et al., *Proc. Natl. Acad. Sci. USA* 95:11532, 1998; etc. Furthermore, a variety of mass spectrometers that are capable of producing spectra of polypeptides with mass accuracies in these preferred ranges are available commercially, e.g., without limitation, the APEX III™ mass spectrometer from Bruker Daltonics of Billerica, Mass.; the HiResESI™ mass spectrometer from IonSpec of Lake Forest, Calif.; the Q-Tof Ultima™ mass spectrometer from Micromass of Milford, Mass.; the API QSTAR™ mass spectrometer from MDS Sciex of Concord, Canada; the AccuTOF™ mass spectrometer from JEOL of Peabody, Mass.; the AXIMA-QIT™ or AXIMA-MALDI TOF™ mass spectrometers from Shimadzu Biotech of Pleasanton, Calif.; etc.

In certain embodiments, the U and F spectra are also obtained under conditions of high mass resolution. The mass resolution specification of a mass spectrometer provides a measure of its ability to resolve polypeptides that have similar molecular weights. In general, the mass resolution depends on both the type of analyzer and the experimental conditions. For the purposes of the present invention, the resolution in a given spectrum is defined as the experimentally determined ratio of the mass of an isolated singly charged peak divided by its full width at half the maximum height (FWHM). For example, if the FWHM values for a singly charged peak at m/z value of 1,658.752 is 0.237, then the resolution of that peak is equal to: $1{,}658.752/0.237 \sim 7{,}000$. Again it will be appreciated that the accuracy and completeness of the analysis will improve as the mass resolution is increased. As with mass accuracy, the mass resolution that is required may depend on the nature of the sample of interest and on the nature of the polypeptides within the sample, e.g., the average molecular weight and/or the range of molecular weights of the polypeptides. In certain embodiments and without limitation, the spectrometer or spectrometers that are used to obtain the U and F spectra may be operated under conditions that are sufficient to resolve isotopes of a singly, preferably doubly, more preferably triply, and even more preferably quadruply charged ion. On a practical level, this will require a resolution of about 2,400 at m/z values of about 300 and a resolution of about 15,000 at m/z values of about 2,000. Overall, mass resolutions of at least 6,000 and more preferably 10,000 or more are desirable.

In general, the U and F spectra within each set of spectra are obtained using the same sample or different aliquots of the same sample. As defined herein different "aliquots" of the same sample have substantially the same polypeptide compositions, e.g., they are obtained by dividing a sample into two or more volumes. Preferably, the U and F spectra in a given set are also obtained using the same spectrometer. In certain embodiments the spectra are obtained back to back to provide the strongest mass accuracy correlation between the U and F spectra. Although the use of a single spectrometer is preferred, it will be appreciated that the U and F spectra may be obtained using two or more spectrometers operating under similar, preferably near identical conditions, e.g., with mass accuracies that differ by less than a factor of 10, 5, 4, 3, or 2. In certain preferred embodiments, the U and F spectra are obtained using a single-stage spectrometer, preferably the same single-stage spectrometer.

Each U and F spectrum in a given set may correspond to a single spectral acquisition or to a summation over two or more spectral acquisitions. In certain preferred embodiments, when several spectra are summed to produce a U or F spectrum, the individual spectra are stored in addition to (or instead of) the summed spectrum since the individual spectra may be used for later analysis. When several acquisitions from the same spectrometer are summed to produce U and F spectra it will be appreciated that these may be obtained sequentially (e.g., $U_1$, $U_2$, $U_3$, etc. followed by $F_1$, $F_2$, $F_3$, etc.), in an interleaved manner (e.g., $U_1$, $F_1$, $U_2$, $F_2$, $U_3$, $F_3$, etc.), or some combination thereof (e.g., $U_1$, $U_2$, $F_1$, $F_2$, $U_3$, $U_4$, $F_3$, $F_4$, etc.). In addition, several spectra obtained over a range of fragmentation energies may be summed to create an F spectrum without having to choose one specific fragmentation energy at the time of data acquisition. Additionally or alternatively, several spectra obtained with two or more different fragmentation mechanisms may be summed to create an F spectrum. Acquisition of U or F spectra will generally be correlated with the fragmentation conditions that are present within the spectrometer. In certain embodiments, the acquisition of U and F spectra may be synchronized with transitions in these fragmentation conditions, e.g., changes in fragmentation energy. In particular, synchronization may prove advantageous in preventing the cross-contamination of unfragmented and fragmented masses between U and F spectra. In certain embodiments, a dead time may be placed in between acquisitions of U and F spectra to further prevent such cross-contamination.

In general, the particular choice in acquisition set up will depend on a number of factors including the nature of the sample, whether the U and F spectra are being obtained with a single-stage spectrometer or a multi-stage spectrometer, whether the U and F spectra are being obtained with the same spectrometer, whether several different samples are being analyzed in succession (e.g., in an LC-MS set up), the spectral acquisition time, the signal-to-noise ratio, the time required to toggle the fragmentation mechanism on and off, the energy and nature of the fragmentation mechanism, the time required to adjust the fragmentation energy, etc.

It is further to be understood that the methods described herein may be modified to analyze sets of spectra that include more than one U spectrum and/or more than one F spectrum. It will be appreciated, for example, that the set of spectra for a given sample may include two or more F spectra that have been obtained with different fragmentation energies and/or two or more F spectra that have been obtained using different fragmentation mechanisms. In particular, as is well known in the art, different fragmentation energies and mechanisms tend to produce different types of F ions (e.g., see Papayannopoulos, *Mass. Spectrom. Rev.* 14:49, 1995). Accordingly, consideration of masses from a collection of F spectra that have been obtained with different energies and/or mechanisms may provide broader coverage across the different fragment ion series (i.e., the a, b, c, x, y, and z series).

As mentioned earlier, it is yet further to be understood that the inventive methods may be used alone or may be used in tandem with other more traditional polypeptide mass fingerprinting techniques (e.g., those described in the prior art). In particular, it may prove advantageous to use the inventive methods to analyze a subset of masses that were unexplained by an earlier method.

Analyzing U and F Spectra

In general, once the U and F spectra in a given set have been obtained (i.e., for a given sample), the methods described herein involve examining the masses in the one or more F spectra (i.e., corresponding to fragments of polypeptides) and attempting to match them with a mass in the one or more U spectra (i.e., corresponding to an unfragmented polypeptide). An F mass is said to match a U mass if it corresponds to a fragment that was generated from the polypeptide that corresponds to the U mass. As described in greater detail below, in certain embodiments, the collection of F masses that have been matched with a U mass are then used to determine an amino acid sequence for the polypeptide that corresponds to the U mass. In certain other embodiments, they are used to determine a set of alternative amino acid sequences for the corresponding polypeptide. In yet other embodiments, they are used to determine the nature, location and relative levels of various modifications within the corresponding polypeptide.

Making a "Formula Call" for a Mass

In a number of embodiments, the processing steps that are used to match F masses with U masses involve making a "formula call" on a candidate mass, e.g., an F mass or a mass differential between two F masses. As defined herein, performing a "formula call" on a candidate mass involves treating amino acid monomers and terminal groups (i.e., $R_N$ and $R_C$ in FIGS. 1 and 2) as "elements" and using their theoretical masses to identify one or more "empirical amino acid formulae" that match the candidate mass. For example, the empirical amino acid formula of a $b_2$ ion (see FIG. 2) that includes a proton as an N-terminal group (i.e., $R_N$=H in FIG. 2), a glycine and a methionine is H-(Gly, Met). Equally, the empirical amino acid formula of an amino acid "stretch" between the $b_2$ ion above and a $b_4$ ion in the same series that includes a proton as an N-terminal group, two glycines, a methionine, and a tyrosine is (Gly, Tyr).

It will be appreciated that all mass calculations and comparisons in this invention must take into account the mass accuracy of the instrument performing the measurement. In general, a mass (measured, theoretical, or combination thereof, e.g., the resultant of some addition or subtraction) is said to "match" a measured mass as long as it falls within the range of actual mass possibilities around the measured mass.

With respect to formula calls, an empirical amino acid formula whose theoretical mass falls outside the range of actual mass possibilities around a candidate measured mass is considered to not "match". Conversely an empirical amino acid formula whose theoretical mass falls within the range of actual mass possibilities around a candidate measured mass is considered to "match". Thus, a formula call can conceivably have, zero, one or more answers. Although formula calls that yield a single empirical formula are preferred, formula calls that yield two or more solutions are not entirely useless since they may lead to a single solution when combined with a separate formula call or other determination. For the purposes of the present application and without limitation, a formula call that yields a single empirical amino acid formula for the measured mass of an F ion is termed a "successful formula call". It will be appreciated that a "successful formula call" provides (a) the amino acid composition of the F ion (e.g., one glycine and one methionine in the above example), (b) the series type of the F ion (e.g., b series in the above example), and (c) the position of the F ion within that series (e.g., position 2 in the above example).

In general, the computational complexity of formula calls increase as the candidate mass is increased. Accordingly, in certain preferred embodiments, an attempt is made to minimize the masses for which formula calls are performed. As described in greater detail below, this is typically achieved by selecting specific ranges of masses to be examined. For example, in certain embodiments, formula calls may be limited to candidate masses that are greater than 50 Da and smaller than 1000, 500, 400, 350, 300, 250, or 200 Da.

The ability to determine an empirical chemical formula (e.g., $C_2H_7ON$) for a molecule based on its measured mass using the theoretical masses of some or all of the chemical elements (e.g., C, H, O, and N in $C_2H_7ON$) is well understood and widely practiced. The MFCalc™ software program that is made freely available by James E. Deline includes an exemplary algorithm. In certain embodiments, formula calls may be achieved using these known techniques in combination with the theoretical masses of amino acid monomers and terminal groups (i.e., instead of the theoretical masses of chemical elements).

Additionally or alternatively, formula calls may be achieved by consulting one or more databases of theoretical masses. The methods described herein are in no way limited to consulting specific databases of theoretical masses. For example, at one extreme, the inventive methods may be used in combination with relatively simple databases that include the theoretical masses (e.g., the monoisotopic masses or some isotopic distribution of masses) of the twenty commonly occurring amino acid monomers (i.e., those listed in Appendix A). Another simple database might cover the commonly occurring $a_2$, $b_2$, $c_2$, $x_2$, $y_2$, and $z_2$ type ions (i.e., a, b, c, x, y, or z type ions that include two amino acid monomers from Appendix A). These relatively simple databases may be supplemented with or used in combination with larger and more complex databases, such as but not limited to, databases that include larger ions (e.g., ions that include 3, 4, 5, 6, 7, 8, 9, 10, etc. amino acid monomers); databases that include less commonly occurring amino acid monomers (e.g., those listed in Appendix B); and/or databases that include alternative N-terminal or C-terminal groups (e.g., those listed in Appendix C). In addition, as described in greater detail in the following, in certain embodiments the databases may further take into account one or more modifications that are known to occur during polypeptide synthesis (e.g., without limitation those listed in Appendix E); post-translational protein modifications (e.g., without limitation those listed in Appendix F); and/or modifications that commonly occur within mass spectrometers as a consequence of the ionization and or detection process, e.g., loss of $H_2O$, loss of $NH_3$, loss of common side chains, etc.

In general, one of ordinary skill in the art will further readily appreciate that suitable databases can be constructed in a variety of ways. One approach might involve determining theoretical masses using the empirical chemical formulae of the molecules in the database in combination with elemental atomic masses (e.g., from Audi and Wapstra, *Nuclear Physics A*, 595:409, 1995), elemental atomic weights (e.g., from Coplen, *Pure Appl. Chem.*, 73:667, 2001), and/or isotopic abundance data (e.g., from Rosman and Taylor, *J Phys. Chem. Ref Data*, 27:1275, 1998). Alternatively and more efficiently, databases may be constructed by performing "reverse" formula calls, i.e., by treating the amino acid monomers and terminal groups as "elements" with specific theoretical masses (e.g., those listed in Appendices A, B, and C) and then applying formulae that calculate the masses of the various empirical amino acid formulae in the database using the masses of these "elements" (e.g., for a, b, c, x, y, or z type ions by using the formulae provided in Appendix D). The latter approach is preferable since it reduces the computational complexity of the database construction process. It is to be understood that the Appendices are provided purely for illustrative purposes and that the methods described herein are in no way limited to using the exact theoretical masses that are provided in the Appendices.

Pre-processing of U and F Spectra

Returning now to the U and F spectra, in certain embodiments, the computational complexity of the inventive methods may be reduced by pre-processing the U and/or F spectra before the U and F masses are examined. This optional pre-processing of the spectra may involve one or some combination of the following approaches or equivalents thereof:

(a) Deconvolving the U and/or F spectra. Deconvolving a mass spectrum involves converting the m/z values in the spectrum to uncharged masses (or "neutral masses"). The methods described herein are independent of the deconvolving algorithm that is used to pre-process the U and/or F spectra. For example, non-limiting algorithms that may be used include those described by Zhang and Marshall, *J Am. Soc. Mass Spectrom.* 9:225, 1998; Wehofsky and Hoffmann, *J. Mass Spectrom.* 37:223, 2002; those described in U.S. Pat. Nos. 5,130,538; 5,581,080; and 5,686,726 to Fenn et al. or U.S. Pat. No. 6,104,027 to Gee et al.; etc.

(b) Deisotoping the U and/or F spectra. In general, deisotoping a mass spectrum involves identifying m/z values that are associated with different isotopic forms of the same ion and associating them with a single m/z value. In certain embodiments, the m/z values of the various isotopic forms are stored since they may be used for later analysis. The methods described herein are independent of the deisotoping algorithm that is used to pre-process the U and F spectra. For example, a non-limiting algorithm that may be used is described by Horn et al., *J Am. Soc. Mass Spectrom.* 11:320, 2000. In preferred embodiments, the m/z values of the different isotopic forms are associated with the monoisotopic mass of the ion. For a given ion, the monoisotopic mass corresponds to the mass of the isotopic form whose elemental composition is composed of the most abundant isotopes of those elements (e.g., $^{12}C$, $^{1}H$, $^{16}O$, $^{14}N$, and $^{32}S$). By definition, the monoisotopic peak is always the lightest peak in a particular isotopic distribution.

(c) Removing from consideration any U masses that are also present in F spectra (e.g., corresponding to fragmented ions detected in the U spectrum). This optional step ensures that the U masses that are used for further analysis do not include masses from fragmented ions. It will be appreciated that this optional step may inadvertently delete the masses of genuine unfragmented ions from the U spectrum, e.g., when relatively low fragmentation energies are used in obtaining F spectra and the likelihood of detecting unfragmented ions in F spectra is therefore relatively high. However, it will be appreciated that this step may prove advantageous when relatively high fragmentation energies are used in obtaining F spectra (i.e., when the likelihood of detecting unfragmented ions in F spectra is relatively low). It may therefore prove advantageous to flag the U masses instead of removing them entirely from consideration. According to such embodiments, the flagged U masses are initially removed from consideration but may be optionally used after the unflagged U masses have been analyzed.

(d) Removing from consideration any F masses that are also present in the U spectrum (e.g., corresponding to unfragmented ions detected in F spectra). This optional step ensures that the F masses that are used for further analysis do not include masses from unfragmented polypeptides. It will be appreciated that this optional step may in certain embodiments inadvertently delete the masses of genuine fragmented ions, e.g., when fragments are accidentally generated as a consequence of the ionization or detection mechanism used to obtain the U spectrum, in certain embodiments it may therefore prove advantageous to flag the F masses instead of removing them entirely from consideration. According to such embodiments, the flagged F masses are initially removed from consideration but may be optionally used after the unflagged F masses have been analyzed.

Once the U and F spectra have been obtained and optionally pre-processed as described above, the F masses are matched with U masses using one or more of the processing steps that are described in detail below. It is to be understood, and it will be readily apparent to one of ordinary skill in the art, that the matching procedure does not (a) require that each of the following processing steps be used or (b) require that the processing steps be used in the order presented. Further it will be appreciated that a given processing step may be repeated several times during the matching procedure, e.g., on either side of a different processing step. In particular, it is to be understood that the following describes a single exemplary embodiment of the matching procedure and that the inventive methods are in no way limited to this particular combination and order of processing steps. Further, for purposes of clarity only and without limitation, the following description of the various processing steps assumes that the U and F spectra have been deconvolved and deisotoped.

Processing step 1: Identifying "Seed" F Masses

According to certain embodiments, the matching procedure may begin by identifying a collection of "seed" F masses that match a particular U mass. As defined herein, identifying a "seed" F mass requires determining the fragment series type of the corresponding F ion (i.e., whether the corresponding F ion belongs to an a, b, c, x, y, or z type ion series). In certain embodiments, the position of the corresponding F ion within the determined series is also determined (e.g., whether the corresponding F ion is a $b_1$, $b_2$, $b_3$, $b_4$, $b_5$, etc. ion if it belongs to a b series). In yet other embodiments, the amino acid composition of the corresponding F ion is also determined (e.g., whether the corresponding F ion includes two glycines or a glycine and a tryptophan if it is a $b_2$ ion). It will be appreciated that in certain embodiments the position and amino acid composition of the F ion may only be approximately defined, e.g., consider a $b_2$ ion that includes amino acid X and asparagine and a $b_3$ ion that includes X and two glycines—these will have near degenerate masses. For example, "seed" F masses may be identified using one or some combination of the following approaches or equivalents thereof:

(a) By identifying an F mass at the low mass end of a series that matches a U mass. In one exemplary embodiment, this may be accomplished by performing a formula call for each F mass that lies within the range of possible two monomer ions in the a, b, c, x, y, or z series. When analyzing polypeptides that include commonly occurring amino acid monomers only, the range will typically be between the theoretical mass of an $a_2$ ion containing two glycines and that of an $x_2$ ion containing two tryptophans. Valid answers will represent two monomer ions. Once a successful formula call has been made, an attempt is made to match the candidate two monomer F mass to a U mass by subtracting the mass of the candidate from each U mass in turn and looking in the F spectral masses for the resulting mass. If found, this second F mass represents the corresponding ion in the series (e.g., $b_2$ and $y_{n-2}$) and it can be matched with the specified U mass. It is to be understood that this approach can be extended to scan for suitable F masses within larger ranges, e.g., for F masses that lie within the range of possible 3, 4, 5, 6, 7, etc. monomer ions in the a, b, c, x, y, or z series. In certain embodiments, the formula calls may be limited to F masses that are greater than 50 Da and smaller than 1000, 500, 400, 350, 300, 250, or 200 Da in order to reduce computational complexity.

(b) Identifying an F mass at the high mass end of a series that matches a U mass. One possible method for accomplishing this might involve selecting a given U mass ($U_i$), selecting an F mass ($F_j$) in the range between $U_i$ and [$U_i$–(mass of heaviest possible two monomer ion)], subtracting the masses $U_i$–$F_j$, and attempting to make a formula call on the result. When analyzing polypeptides that include commonly occurring amino acid monomers only, the mass of the heaviest possible two monomer ion will typically be that of an $x_2$ ion containing two tryptophans. This process can be repeated with other F masses that lie within the range until a successful formula call is made. A successful formula call will indicate a match and will provide both the ion type of the fragment corresponding to the resultant mass (i.e., $U_i$–$F_j$) and the fragment corresponding to the selected F mass ($F_j$). In certain embodiments this matching procedure may be confirmed by looking in the F spectral masses for the resultant mass (i.e., $U_i$–$F_j$). It will be appreciated that this approach can be extended to scan for suitable F masses within larger ranges, e.g., in the range between $U_i$ and [$U_i$–(mass of heaviest possible 3, 4, 5, 6, 7, etc. monomer ion)]. Again, in certain embodiments, formula calls may be limited to masses that are greater than 50 Da and smaller than 1000, 500, 400, 350, 300, 250, or 200 Da in order to reduce computational complexity.

(c) Finding arbitrary pairs of F masses that match a U mass. This is done by searching for pairs of F masses that sum to a U mass. One possible method for accomplishing this may involve selecting a given U mass ($U_i$), finding the largest F mass that is less than $U_i$, subtracting it from $U_i$ and looking to see if a second F spectral mass matches the resultant mass. If there is, the two F masses represent a pair that match $U_i$. One could then proceed in this fashion testing the next lighter F mass until the median of the mass range (i.e., between the lightest possible F mass and $U_i$) is reached. The process could then be repeated using a different U mass. One of ordinary skill in the art will appreciate numerous variations and alternatives to this approach, e.g., one could select a given U mass ($U_i$), find the smallest F mass, subtract its mass from that of $U_i$ and look to see if there is another F mass which has that mass. In certain embodiments, once a pair of F masses has been matched with a U mass, an attempt is then made to identify the series type of the corresponding F ions, i.e., whether they belong to an a, b, c, x, y, or z series. According to the methods described herein, this is done by performing a formula call on the lighter F mass in the matched pair. At most one should be successful. As with approaches (a) and (b) above, these formula calls may, in certain embodiments, be limited to masses that are greater than 50 Da and smaller than 1000, 500, 400, 350, 300, 250, or 200 Da. The ion type of the heavier matched F ion will be complementary to the ion type of the lighter matched F ion in the same pair (e.g., $b_2$ and $Y_{n-2}$).

It is to be understood that in certain embodiments, large seed F masses (e.g., without limitation F masses that lie within 1000, 500, 400, 350, 300, 250, or 200 Da of the matched U mass) that are matched according to (a), (b), or (c) above may be removed from the list of F masses for match against a different U mass. Indeed, in certain embodiments, large seed F masses that have been matched with a U mass will not be statistically likely to match for a different U mass. In general, but not necessarily, the smaller seed F masses should not be removed from further consideration as they may correspond to a fragment that has been generated from multiple U ions. The decision to remove matched seed F masses from consideration will typically depend on the number of U masses that were obtained from the original sample and hence on the complexity of the original sample.

Processing Step 2: Extending a Seeded Ion Series Using Next Adjacent Ions

In certain embodiments, once a collection of seed F masses have been identified, the inventive methods may involve extending one or more of the seeded ion series by identifying the F masses of ions that are adjacent to a seed ion in the series. This may be accomplished by looking for F masses at each of the theoretical masses for adjacent ions in a seeded ion series. For example, in certain embodiments, this may involve adding or subtracting the theoretical mass of one, some or all of the possible amino acid monomers (e.g., those listed in Appendices A and B) from the theoretical ion mass that corresponds to the measured mass of the seed ion and then looking in the F spectral masses for a match. Using the theoretical mass of the seed ion in this step (and in other steps discussed below) as opposed to the measured mass prevents problems that might occur with accumulated errors in measurement. Although less preferable, it is to be understood that one may use the measured mass of the seed ion in this and later steps. In general, it is to be understood that absent an explicit reference to "theoretical mass" or "measured mass" any occurrence of the terms "mass of a fragment" or "mass of an ion" in the specification or claims encompasses the use of theoretical or measured masses. It will be appreciated that this step can be repeated using the growing or shrinking seed ion each time an amino acid monomer has been added or removed from the original seed ion.

Processing Step 3: Extending a Seeded Ion Series by Scanning Ahead

In certain embodiments, the seeded ion series may additionally (or alternatively) be extended by identifying F masses of ions that are separated from a seed ion by two or more amino acid monomers. This approach will be particularly useful if the mass corresponding to the next ion in a series is missing from the F spectral masses (for example, if there is a mass for an $a_3$ ion, but no mass for the $a_4$ ion has been detected). This can be done using one or some combination of the following approaches or equivalents thereof:

(a) Identifying the maximum (or minimum) possible mass of the g+h (or g−h) monomer ion in the seeded series (where g is the series position of the last identified ion and h is the number of ions believed to be missing, e.g., 1, 2, 3, 4, 5, 6, 7, etc.). For each F mass between the last identified series ion and the maximum (or minimum) possible mass, one may subtract the theoretical mass of the last identified ion (or subtract each F mass from the theoretical mass of the last identified ion). A formula call is then made on the resulting mass. For most F masses, there will be no answer. Answers within the mass accuracy of the instrument indicate that the F mass in question is potentially part of the series and provide the composition of the missing amino acid monomers.

(b) If F ions from the same series have already been identified on the other side of the gap via other methods (e.g., via processing step 1 and/or 2), one might examine all F spectral masses that lie between [(theoretical mass of the lighter identified ion)+(theoretical mass of the lightest monomer)] and [(theoretical mass of the heavier identified ion)−(theoretical mass of the lightest monomer)]. One could then either subtract the theoretical mass of the lighter identified ion from the mass of the candidate F ion or subtract the mass of the candidate F ion from the theoretical mass of the heavier identified ion (whichever result is smaller) and make a formula call on the result. For most F masses, there will be no answer. Answers within the mass accuracy of the instrument indicate that the F mass in question is potentially part of the series and provide the composition of the missing amino acid monomers.

Processing Step 4: Identifying F Masses in the Same Position as a Seed F Mass in an Adjacent Series According to certain embodiments, additional F masses may be matched with a U mass by identifying F masses that correspond to an ion in the same position as a seed ion but in an adjacent series (e.g., $b_2$ or $c_2$ when the seed ion is $a_2$). This can be accomplished by adding or subtracting one, some or all of the possible series offset masses from the theoretical ion mass that corresponds to the measured mass of the seed ion and then looking in the F spectral masses for a match. The series offset masses represent the mass deltas between the series of the seed ion (e.g., the a series) and the other related series (e.g., the b and c series). As is well known in the art and as will be readily appreciated by considering the chemical formulae in FIG. 2 and the formulae in Appendix D, the series offset mass between the b and a series corresponds to the mass of a CO group; the series offset mass between the b and c series corresponds to the mass of an $NH_3$ group; etc.

Processing Step 5: Validating a Seeded Ion Series

In general, once a collection of related series have been extended (i.e., for a particular U mass) they may be optionally validated using one or some combination of the following approaches or equivalents thereof:

(a) Whenever corresponding members of related series have been identified (e.g., $b_2$ and $y_{n-2}$) the sum of their theoretical masses should match the measured U mass within the mass accuracy of the instrument.

(b) If multiple ions representing the same adjacent amino acid positions on different series are present (e.g., $b_2$, $b_3$, $C_2$, and $C_3$), a formula call for the mass delta between the heavier and lighter ions in the same series (e.g., $b_3-b_2$ and $c_3-c_2$) should match to the same amino acid monomer.

(c) If multiple ions representing the same non-adjacent amino acid positions on different series are present (e.g., $b_2$, $b_5$, $c_2$, and $c_5$), a formula call for the mass delta between the heavier and lighter ions in the same series (e.g., $b_5-b_2$ and $c_5-c_2$) should match to the same combination of amino acid monomers.

(d) The measured isotope distribution for a given F ion should match the theoretical isotope distribution for the ion calculated from its empirical amino acid formula. This step requires analyzing F spectra prior to any deisotoping.

(e) In general, the signal intensity for a given F ion should not exceed the signal intensity of the parent U ion.

Processing Step 6: Creating One or More Amino Acid Sequences for a U Ion

Once a collection of F masses in one or more fragment series for a given U ion have been matched and optionally validated, a set of possible amino acid sequences for the U ion can be created. First, the one or more fragment series are individually traversed and the amino acid monomer representing the difference in mass between adjacent ions in each series is identified via a formula call. It will be appreciated that this step may be shortened by using the results of processing steps 2 and 5 if they were performed.

In certain embodiments, it may prove advantageous at this stage of processing to construct a consensus amino acid sequence by comparing the amino acid monomers that are predicted in different series to determine whether they add the same amino acid monomer to the same position in the sequence. In cases where next adjacent ions are missing from a particular position in one of the matched series (e.g., $a_4$ when $a_5$ has been matched), the monomer at that position may be determined by examining a different series that includes that particular pair (e.g., $b_4$ and $b_5$). If next adjacent ions for a particular pair of positions (e.g., positions 4 and 5) have not been identified in a single of the matched series, then the appropriate monomer may be determined by taking into account series offsets and performing a formula call on the mass delta between ions from next adjacent positions on two different series (e.g., $b_4$ and $a_5$). If none of the series have identified an ion at a given point in the series (e.g., position 4), then sets of alternative sequences are prepared, where the amino acid composition determined from the mass delta that spans that position (e.g., between $a_3$ and $a_5$) is represented in all possible permutations (and optionally all possible combinations if a formula call for the mass delta yields several solutions). Where exact amino acid calling is not possible due to identical mass (e.g., leucine vs. isoleucine) sets of alternative sequences are also prepared.

Accounting for Polypeptide Modifications

In certain embodiments, for example when analyzing polypeptide samples that have been produced by chemical synthesis, it may prove advantageous to expand the methods described herein to take into account one or more of the theoretical mass deltas that may occur as a consequence of modifications during polypeptide synthesis (e.g., without limitation those listed in Appendix E). Similarly, when analyzing samples that have been extracted from a natural source (e.g., a cell extract) it may prove advantageous to take into account one or more of the theoretical mass deltas that are known to be caused by certain post-translational protein modifications (e.g., without limitation those listed in Appendix F). Chemical and/or enzymatic processing of samples may also introduce modifications. Yet further, according to certain other embodiments one may wish to take into account theoretical mass deltas that commonly occur within mass spectrometers as a consequence of the ionization and or detection process, e.g., loss of $H_2O$, loss of $NH_3$, loss of common side chains, etc.

In certain embodiments, the formula calling technique may be expanded to take into account one, some or all of the theoretical mass deltas of interest. For example, the databases of theoretical masses may be expanded to include a sub-set of relevant theoretical mass deltas. Alternatively, when traditional techniques for determining empirical formula are being used with amino acid monomers and terminal groups as "elements", the theoretical mass deltas may be included as additional "elements". In general, the choice of modifications that need to be considered will depend in part on the nature of the sample. The U and F spectral masses are then analyzed as described above, but formula calls are performed using these additional "elements" and/or expanded databases. Alternatively, the U and F spectral masses may be analyzed as described previously (i.e., without taking into account possible modifications) and then by post-processing the resulting data using one or some combination of the following approaches or equivalents thereof:

(a) Identifying ions on either side of discontinuities in one or more ion series. Modifications will be represented by a shift in the mass of the F ions at the point of modification in the series. Based on the previously described methods (i.e., those that do not take into account the possibility of modifications) a modification will therefore generally cause an unresolvable gap in the ion series. It is worth noting that according to certain embodiments (e.g., when a polypeptide with the modification and the same polypeptide without the modification are both present in the sample that is used to obtain a given set of U and F spectra) the gap may not occur. Indeed, according to such embodiments each offset mass (i.e., the mass of an F ion from the modified polypeptide) would occur together with a corresponding non-offset mass (i.e., the mass of the corresponding F ion from the unmodified polypeptide). It will be appreciated that the co-occurrence of modified and unmodified polypeptides in the same sample will depend on the nature of the modification, the nature of the sample, and the extent of any separations done subsequent to the modification and prior to mass analysis, e.g., in the form of an MDLC separation. In general, gaps can be identified as a discontinuity in an ion series that is approached from both ends (e.g., $y_{n-4}$ cannot be found when extending a series from heavier to lighter and $y_{n-3}$ cannot be found when extending a series from lighter to heavier). The gaps can also be identified by looking for any two series that break at the same point (e.g., b and y series). When such a gap cannot be explained by the methods previously described, it becomes a candidate for the site of a modification.

Some modifications have well known mass deltas (e.g., without limitation those listed in Appendices E and F). These can be tested for by taking the mass represented by the gap, subtracting in turn the mass of one, some or all of the possible modifications with known mass deltas and attempting to perform a formula call on the result. A definitive call represents a modification of that type and an identification of the amino acid monomer present at that point in the sequence. In cases where an ion is missing adjacent to the point of modification, a group of amino acid monomers will be identified in the formula call. The amino acid monomer or monomers at that location can be verified by determining whether they are compatible with the identified modification. The nature of the modification may help identify the relative order of the amino acid monomers in the series if one is compatible with the modification and the other is not.

(b) Testing for modifications with known mass deltas when ions have not been identified on both sides of the gap. One way this can be done involves adding (when extending from lighter to heavier) or subtracting (when extending from heavier to lighter) the mass of possible modifications from the theoretical mass of the ion below (or above) the discontinuity, and then searching for the next ion in the series using previously taught methods as if the ion below (or above) the discontinuity had the resultant mass. A successful search identifies the correct amino acid at that position and identifies the modification.

Accounting for Mass Tagging

In certain embodiments, the methods described herein may be modified to take into account the use of mass tagging techniques, e.g., for differential quantitation of proteins in different samples. For example, for purposes of illustration and without limitation the methods may be modified to take into account the use of isotope-coded affinity tags (ICAT). Briefly, ICATs are a class of reagents, which are built of three main sections, namely an affinity tag, a linker for incorporation of stable isotopes, and a reactive group with specificity toward the thiol groups that are present in cysteines (e.g., see Gygi et al., Nat. Biotech. 17:994, 1999). A heavy form (e.g., containing deuteriums on the carbon backbone) and a light form (e.g., with no deuteriums) of ICAT reagents are used in the labeling of proteins in different samples. The method typically consists of four steps, for example:

(a) The light form of the ICAT reagent is used to derivative cysteine side chains in a first protein sample (e.g., representing a first cell state). The heavy form of ICAT is used to derivatize the same protein in a different sample (e.g., representing a second cell state).

(b) The two samples are mixed and digested, forming a mixture of polypeptides of which some are tagged (i.e., those containing a cysteine).

(c) Avidin affinity chromatography is used to isolate the tagged fragments.

(d) The isolated polypeptides are then separated using MDLC and fed into a mass spectrometer for analysis.

The quantitative information comes from measuring and comparing the relative signal intensities of the pair of chemically identical polypeptides labeled with the light and heavy forms of the ICAT. The ratio of the polypeptide pairs provides quantitative information on the original protein of interest. This is due to the fact that the polypeptide fragments represent the ratio of the original amounts of the proteins in, for example, first and second cell states.

When using mass tags such as ICATs, certain polypeptides will result in two peaks in the U spectra (e.g., those containing a cysteine), offset by the mass delta between the light and heavy forms of the tag. Matching pairs of F masses to a U mass will be unaffected since the total number of mass tags on the U ion will be divided between the pair in the F series so the sum should agree as normal. However, when making sequence calls the mass of selected amino acid monomers will be different (due to the addition of the mass tag). There will actually be multiple masses for these amino acid monomers: untagged due to incomplete reaction, tagged with a light tag and tagged with a heavy tag. The formula calling algorithm will therefore need to take this into account. The addition of a tag is effectively equivalent to a post-translational modification at the site where the tag exists. When extending the ion series, it can be treated as such. The presence of a tag also provides verification of the called empirical amino acid formula as only select amino acid monomers will react with the tag (e.g., cysteines in the example provided).

One having ordinary skill in the art will readily appreciate that this approach can be applied with other differential isotope tagging techniques (e.g., see Goshe et al., Anal. Chem. 73:2578, 2001; Yao et al., Anal. Chem. 73:2836, 2001; etc) and more generally any mass tagging technique (e.g., see the review by Smith et al., OMICS 6:61, 2002).

Devices

One have ordinary skill in the art will readily recognize that while the certain embodiments have been described in the context of inventive methods, the present invention also encompasses devices that may be used in implementing the inventive methods. The foregoing processing steps described herein may be performed in a computer system executing machine instructions produced using any one or more of a variety of different techniques.

In one embodiment, the machine instructions may be produced using software including, for example, a programming language, third party software package, routines included as part of an operating system, and the like. The machine instructions, or a form thereof, may be stored in a computer program product that includes a computer readable medium (e.g., without limitation a floppy disk, a hard disk drive, a RAM, a CD-ROM, a tape, a cassette, etc.) with a set of machine executable instructions for performing the various steps of the inventive methods. The software is then loaded into a computer system (e.g., an offline computer or an online computer that also runs the mass spectrometer) using a removable storage drive, a hard drive, or a communications interface. The software, when executed by one or more processors within the computer system, causes the processors to perform the functions of the invention as described herein. It should be noted that the foregoing may also be implemented in hardware using, for example, hardware components such as application specific integrated circuits. An embodiment may also implement the foregoing using a combination of hardware and/or software.

Other Embodiments

Other embodiments of the invention will be apparent to those skilled in the art from a consideration of the specification or practice of the invention disclosed herein. In particular, it will be appreciated by one having ordinary skill in the art that the methods described herein may also be used to identify polynucleotides or polysaccharides.

As used herein, a "polynucleotide" is a polymer of nucleotides, typically comprising at least two nucleotides linked together by phosphodiester bonds. The terms "polynucleotide", "oligonucleotide", and "nucleic acid" may be used interchangeably. DNA and RNA are exemplary polynucleotides that could be analyzed. Without limitation, the present invention also encompasses the analysis of peptide nucleic acids (PNAs), locked nucleic acid (LNAs), and unstructured nucleic acids (UNAs). As with polypeptides, measured U and F polynucleotide masses are analyzed using the inventive algorithms. Polynucleotides are identified by the sequence of nucleotides that they include. Formula calls are performed using nucleotide monomer "elements" instead of amino acid monomer "elements". In certain embodiments, the theoretical masses of common nucleotides may be used (i.e., nucleotides that include the bases adenine, thymine, cytosine, guanine, or uracil). Additionally or alternatively, the theoretical masses of uncommon or non-naturally occurring nucleotides may be used (e.g., without limitation, nucleotides that include the bases 2-aminoadenine, 2-thiothymine, 3-methyladenine, 5-propynylcytosine, 5-propynyluracil, 5-bromouracil, 5-fluorouracil, 5-iodouracil, 5-methylcytosine, 7-deazaadenine, 7-deazaguanine, 8-oxoadenine, 8-oxoguanine, O(6)-methylguanine, or 2-thiocytosine). Similarly, mass deltas caused by sugar modifications (e.g., 2'-fluororibose, arabinose, hexose, and riboses with a 2'-O, 4'-C-methylene bridge) and/or modified phosphate groups (e.g., phosphorothioates and 5'-N-phosphoramidite linkages) may be considered. As with polypeptides, formula calls for polynucleotide ions will also need to take into account the theoretical masses of the terminal groups, typically these will be hydroxyl or phosphate.

As used herein, a "polysaccharide" is a polymer of sugars, typically comprising at least two sugars. The terms "polysaccharide", "oligosaccharide", and "carbohydrate" may be used interchangeably. The inventive methods may be used to analyze linear or branched polysaccharides. As with polypeptides, measured U and F polysaccharide masses are analyzed using the inventive algorithms. Polysaccharides are identified by the sequence of sugars that they include. Formula calls are performed using sugar monomers "elements" instead of amino acid monomers "elements". In certain embodiments, the theoretical masses of common sugars may be used (e.g., arabinose, ribose, xylose, glucose, fructose, galactose, and mannose). Additionally or alternatively, the theoretical masses of less common or non-naturally occurring sugars may be used (e.g., deoxyribose, fucose, rhamnose, galactosamine, N-acetylgalactosamine, glucosamine, N-acetylglucosamine, glucuronic acid, muramic acid, N-acetylneuraminic acid, N-glycolylneuraminic acid, heptose, etc.). Similarly, mass deltas caused by sugar modifications (e.g., methylation, acetylation, phosphorylation, etc.) may be considered. As with polypeptides, formula calls for polysaccharide ions will also need to take into account the theoretical masses of the terminal groups, typically polysaccharides include free reducing ends or reduced reducing ends.

APPENDIX A

THEORETICAL MASSES OF
COMMONLY OCCURRING AMINO ACID MONOMERS

| AMINO ACID MONOMER | MONOISOTOPIC MASS |
|---|---|
| Alanine | 71.03711 |
| Arginine | 156.10111 |
| Asparagine | 114.04293 |
| Aspartic acid | 115.02694 |
| Cysteine | 103.00919 |
| Glutamine | 128.05858 |
| Glutamic acid | 129.04259 |
| Glycine | 57.02146 |
| Histidine | 137.05891 |
| Isoleucine | 113.08406 |
| Leucine | 113.08406 |
| Lysine | 128.09496 |
| Methionine | 131.04049 |
| Phenylalanine | 147.06841 |
| Proline | 97.05276 |
| Serine | 87.03203 |
| Threonine | 101.04768 |
| Tryptophan | 186.07931 |
| Tyrosine | 163.06333 |
| Valine | 99.06841 |

APPENDIX B

THEORETICAL MASSES OF
LESS COMMONLY OCCURRING AMINO ACID MONOMERS

| AMINO ACID MONOMER | MONOISOTOPIC MASS |
|---|---|
| 2-Aminobutyric acid | 85.05276 |
| Aminomethylcysteine | 146.05138 |
| Carboxyamidomethylcysteine | 160.03065 |
| Carboxymethylcysteine | 161.01466 |
| Cysteic acid | 150.99393 |
| Dehydroalanine | 69.02146 |
| Dehydroamino-2-butyric acid | 83.03711 |
| 4-Carboxyglutamic acid | 173.03242 |
| Homoserine | 101.04768 |
| Hydroxylysine | 144.08988 |
| Hydroxyproline | 113.04768 |
| Isovaline | 99.06841 |
| Norleucine | 113.08406 |
| Ornithine | 114.07931 |
| 2-Piperidinecarboxylic acid | 111.06841 |
| Pyroglutamic acid | 111.03203 |
| Sarcosine | 71.03711 |

APPENDIX C

THEORETICAL MASSES OF
COMMON N-TERMINAL GROUPS

| N-TERMINAL GROUP | MONOISOTOPIC MASS |
|---|---|
| Hydrogen | 1.00782 |
| Formyl | 29.00274 |
| Acetyl | 43.01839 |

THEORETICAL MASSES OF
COMMON C-TERMINAL GROUPS

| C-TERMINAL GROUP | MONOISOTOPIC MASS |
|---|---|
| Hydroxyl | 17.00274 |
| Amide | 16.01872 |

APPENDIX D

FORMULAE FOR CALCULATING THE THEORETICAL MASSES
OF CERTAIN F IONS IN THE A, B, C, X, Y, OR Z SERIES

| F ION TYPE | [1]FORMULA |
|---|---|
| a | [N] + [M] − CO |
| b | [N] + [M] |
| c | [N] + [M] + NH$_3$ |
| x | [C] + [M] + CO |
| y | [C] + [M] + H$_2$ |
| z | [C] + [M] − NH |

[1][N] is the mass of the N-terminal group (e.g., from Appendix C), [C] is the mass of the C-terminal group (e.g., from Appendix C), and [M] represents the summed mass of the amino acid monomers within the fragment (e.g., from Appendices A and B).

APPENDIX E

THEORETICAL MASS DELTAS DUE TO SOME
PROTECTING GROUPS AND SIDE REACTIONS ENCOUNTERED
IN SYNTHETIC POLYPEPTIDE ANALYSIS

| MODIFICATION | Δ MONOISOTOPIC MASS |
|---|---|
| Methyl | 14.01565 |
| Formyl | 27.99491 |
| Ethyl | 28.03130 |
| Acetyl | 42.01056 |
| t-Butyl | 56.06260 |
| Anisyl | 90.04695 |
| Benzyl | 90.04695 |
| Trifluoracetyl | 95.98230 |
| N-hydroxysuccinimide | 97.01638 |
| t-Butyloxycarbonyl | 100.05243 |
| Benzoyl | 104.02621 |
| 4-Methylbenzyl | 104.06260 |
| Thioanisyl | 106.02411 |
| Thiocresyl | 106.02411 |
| Benzyloxymethyl | 120.05751 |
| 4-Nitrophenyl | 121.01638 |
| Benzyloxycarbonyl | 134.03678 |
| 2-Nitrobenzoyl | 149.01129 |
| 2-Nitrophenylsulphenyl | 152.98845 |
| 4-Toluenesulphonyl | 154.00885 |
| Pentafluorophenyl | 165.98419 |
| Diphenylmethyl | 166.07825 |
| 2-Chlorobenzyloxycarbonyl | 167.99781 |
| 2,4,5-Trichlorophenyl | 177.91438 |
| 2-Bromobenzyloxycarbonyl | 211.94729 |
| 9-Fluorenylmethyloxycarbonyl | 222.06808 |
| Triphenylmethyl | 242.10955 |
| 2,2,5,7,8-pentamethylchroman-6-sulphonyl | 266.09767 |

APPENDIX F

THEORETICAL MASS DELTAS DUE TO CERTAIN
POST-TRANSLATIONAL MODIFICATIONS OF PROTEINS

| POST-TRANSLATIONAL MODIFICATION | Δ MONOISOTOPIC MASS |
|---|---|
| Homoserine formed from Met | −29.99281 |
| Pyroglutamic acid formed from Gln | −17.02655 |
| Disulphide bond formation | −2.01565 |
| C-terminal amide formed from Gly | −0.98402 |
| Deamidation of Asn and Gln | 0.98402 |
| Methylation | 14.01565 |
| Hydroxylation | 15.99491 |
| Oxidation of Met | 15.99491 |
| Formylation | 27.99491 |
| Acetylation | 42.01056 |
| Carboxylation of Asp or Glu | 43.98983 |
| Carboxyamidomethylcysteine from Cys | 57.02146 |
| Carboxymethylcysteine from Cys | 58.00548 |
| Phosphorylation | 79.96633 |
| Sulphation | 79.95682 |
| Pyridylethylcysteine from Cys | 105.05785 |
| Cysteinylation | 119.00410 |
| Pentose addition | 132.04226 |

APPENDIX F-continued

THEORETICAL MASS DELTAS DUE TO CERTAIN POST-TRANSLATIONAL MODIFICATIONS OF PROTEINS

| POST-TRANSLATIONAL MODIFICATION | Δ MONOISOTOPIC MASS |
|---|---|
| Deoxyhexose addition | 146.05791 |
| Hexosamine addition | 161.06881 |
| Hexose addition | 162.05282 |
| Lipoic acid addition | 188.03296 |
| N-acetylhexosamine addition | 203.07937 |
| Farnesylation | 204.18780 |
| Myristoylation | 210.19836 |
| Biotinylation | 226.07760 |
| Pyridoxal phosphate addition | 231.02966 |
| Palmitoylation | 238.22966 |
| Stearoylation | 266.26096 |
| Geranylgeranlylation | 272.25040 |
| N-acetylneuraminic acid addition | 291.09542 |
| Glutathionylation | 305.06816 |
| N-glycolylneuraminic acid addition | 307.09033 |
| 5'-Adenosylation | 329.05252 |
| 4'-Phosphopantetheine addition | 339.07797 |
| ADP-ribosylation | 541.06111 |

APPENDIX G

40. The computer program product of claim 39, further comprising: instructions for removing masses from the first dataset that are also present in the second dataset before selecting a mass from the first dataset.
41. The computer program product of claim 39, further comprising: instructions for removing masses from the second dataset that are also present in the first dataset before selecting a mass from the first dataset.
42. The computer program product of claim 39, wherein said instructions for matching masses in the second dataset with the selected mass comprise: instructions for subtracting a first mass from the selected mass to produce a mass delta; and instructions for identifying a second mass in the second dataset that matches the mass delta.
43. The computer program product of claim 42, further comprising: instructions for performing a formula call on the first or second mass.
44. The computer program product of claim 43, wherein said instructions for performing a formula call on the first or second mass are limited to masses below 500 Da.
45. The computer program product of claim 42, further comprising one or a combination of:
    instructions for identifying a mass in the second dataset that differs from the first or second mass by the theoretical mass of one or more monomer units;
    instructions for identifying a mass in the second dataset that differs from the first or second mass by the theoretical mass of one or more monomer units and a biopolymer modification; and
    instructions for identifying a mass in the second dataset that differs from the first or second mass by a theoretical series offset mass.
46. The computer program product of claim 39, wherein said instructions for matching masses in the second dataset with the selected mass comprise: instructions for subtracting a first mass in the second dataset from the selected mass to generate a mass delta; and instructions for performing a formula call on the mass delta.
47. The computer program product of claim 46, further comprising: instructions for identifying a second mass in the second dataset that matches the mass delta.
48. The computer program product of claim 47, wherein said instructions for performing a formula call on the mass delta are limited to mass deltas below 500 Da.
49. The computer program product of claim 47, further comprising one or a combination of:
    instructions for identifying a mass in the second dataset that differs from the first or second mass by the theoretical mass of one or more monomer units;
    instructions for identifying a mass in the second dataset that differs from the first or second mass by the theoretical mass of one or more monomer units and a biopolymer modification; and
    instructions for identifying a mass in the second dataset that differs from the first or second mass by a theoretical series offset mass.
50. The computer program product of claim 49, wherein said instructions for identifying a mass in the second dataset that differs from the first or second mass by the theoretical mass of one or more monomer units comprise: instructions for generating a resultant mass by adding or subtracting the sum of the theoretical masses of one or more possible monomer units to or from the first or second mass; and instructions for identifying a third mass in the second dataset that matches the resultant mass.
51. The computer program product of claim 49, wherein said instructions for identifying a mass in the second dataset that differs from the first or second mass by the theoretical mass of one or more monomer units comprise: instructions for generating a mass delta by subtracting a mass in the second dataset from the first or second mass; and instructions for performing a formula call on the mass delta.
52. The computer program product of claim 51, wherein said instructions for performing a formula call on the mass delta are limited to mass deltas below 500 Da.
53. The computer program product of claim 49, wherein said instructions for identifying a mass in the second dataset that differs from the first or second mass by the theoretical mass of one or more monomer units and a biopolymer modification comprise:
    instructions for generating a first mass delta by subtracting a mass in the second dataset from the first or second mass;
    instructions for subtracting the theoretical mass of a possible biopolymer modification from the first mass delta to produce a second mass delta; and instructions for performing a formula call on the second mass delta.
54. The computer program product of claim 49, wherein said instructions for identifying a mass in the second dataset that differs from the first or second mass by a theoretical series offset mass comprise:
    instructions for generating a resultant mass by adding or subtracting a theoretical series offset mass to or from the first or second mass; and instructions for identifying a third mass in the second dataset that matches the resultant mass.
55. The computer program product of claim 39, wherein said instructions for comparing the matched masses to determine a monomer sequence for the biopolymer with the selected mass comprise:
    instructions for grouping the matched masses according to the series type of their corresponding fragments;
    instructions for calculating mass deltas between pairs of matched masses that correspond to fragments at adjacent positions in a represented series;
    instructions for performing a formula call on the mass deltas;
    instructions for assigning monomers associated with the mass deltas based on the formula call; and
    instructions for determining a monomer sequence for the biopolymer with the selected mass based on said assigning.
56. The computer program product of claim 55, further comprising: instructions for calculating mass deltas between pairs of matched masses that correspond to fragments at non-adjacent positions in a represented series;
    instructions for performing a formula call on the mass deltas; and instructions for assigning combinations of monomers associated with the mass deltas based on the formula call.
57. The computer program product of claim 55, further comprising: instructions for calculating mass deltas between pairs of matched masses that correspond to fragments at adjacent positions on different represented series;
    instructions for performing a formula call on the mass deltas; and instructions for assigning monomers associated with the mass deltas based on the formula call.
58. The computer program product of claim 55, further comprising: instructions for calculating mass deltas between pairs of matched masses that correspond to fragments at non-adjacent positions on different represented series;
    instructions for performing a formula call on the mass deltas; and instructions for assigning combinations of monomers associated with the mass deltas based on the formula call.
59. The computer program product of claim 39, wherein the biopolymer with the selected mass is a polypeptide and the monomer sequence is an amino acid sequence.
60. The computer program product of claim 39, wherein the biopolymer with the selected mass is a polynucleotide and the monomer sequence is a nucleotide sequence.
61. The computer program product of claim 39, wherein the biopolymer with the selected mass is a polysaccharide and the monomer sequence is a sugar sequence.
62. The computer program product of claim 39, wherein the polysaccharide is linear.

APPENDIX G-continued

63. The computer program product of claim 39, wherein the polysaccharide is branched.
64. The computer program product of claim 39, wherein:
    the sample includes a plurality of biopolymers;
    the first dataset includes measured masses of the plurality of biopolymers; and
    the second dataset includes measured masses of a collection of fragments of the plurality of biopolymers.

We claim:

1. A method of identifying a biopolymer in a sample that includes one or more biopolymers, the method comprising:
   selecting a mass from a first dataset, wherein said first dataset includes measured masses of the one or more biopolymers;
   matching masses in a second dataset with the selected mass using a computer, wherein said second dataset includes measured masses of a collection of fragments of the one or more biopolymers, and wherein the matched masses represent fragments of the biopolymer with the selected mass; and
   comparing the matched masses to determine a monomer sequence for the biopolymer with the selected mass.

2. The method of claim 1, further comprising:
   obtaining a first mass spectrum of the one or more biopolymers under conditions that cause the one or more biopolymers to be detected in unfragmented form, wherein said first mass spectrum is used in producing said first dataset; and
   obtaining a second mass spectrum of the one or more biopolymers under conditions that cause the one or more biopolymers to be fragmented into a collection of fragments prior to detection, wherein said second mass spectrum is used in producing said second dataset.

3. The method of claim 2, wherein said first and second mass spectra are obtained consecutively using the same spectrometer and the spectrometer is a single-stage spectrometer.

4. The method of claim 2, wherein the second mass spectrum results from a summation of two different mass spectra obtained with different fragmentation energies.

5. The method of claim 2, wherein the second mass spectrum results from a summation of two different mass spectra obtained with different fragmentation mechanisms.

6. The method of claim 2, further comprising:
   obtaining a third mass spectrum of the one or more biopolymers under conditions that cause the one or more biopolymers to be fragmented into a collection of fragments prior to detection, wherein said third mass spectrum is used in producing said second dataset and said second and third mass spectra are obtained using different fragmentation energies.

7. The method of claim 2, further comprising:
   obtaining a third mass spectrum of the one or more biopolymers under conditions that cause the one or more biopolymers to be fragmented into a collection of fragments prior to detection, wherein said third mass spectrum is used in producing said second dataset and said second and third mass spectra are obtained using different fragmentation mechanisms.

8. The method of claim 1, wherein the masses in the first and second datasets are neutral masses.

9. The method of claim 1, wherein the masses in the first and second datasets are mono isotopic masses.

10. The method of claim 1, further comprising:
    removing masses from the first dataset that are also present in the second dataset before said selecting a mass from the first dataset.

11. The method of claim 1, further comprising:
    removing masses from the second dataset that are also present in the first dataset before said selecting a mass from the rust dataset.

12. The method of claim 1, wherein said matching masses in the second dataset with the selected mass comprises:
    subtracting a first mass from the selected mass to produce a mass delta; and
    identifying a mass in the second dataset that differs from the first or second mass by the theoretical mass one or more monomer units and a biopolymer modification; and
    identifying a mass in the second dataset that differs from the first or second mass by a theoretical series offset mass.

13. The method of claim 12, further comprising: performing a successful formula call on the first or second mass.

14. The method of claim 13, wherein in the step of performing a successful formula call on the first or second mass, the first or second mass is below 500 Da.

15. The method of claim 12, wherein said matching masses in the second dataset with the selected mass further comprises one or a combination of: identifying a mass in the second dataset that differs from the first or second mass by the theoretical mass of a one or more monomer units; identifying a mass in the second dataset that differs from the first or second mass by the theoretical mass of one or more monomer units and a biopolymer modification; and identifying a mass in the second dataset that differs from the first or second mass by a theoretical series offset mass.

16. The method of claim 1, wherein said matching masses in the second dataset with the selected mass comprises: subtracting a first mass in the second dataset from the selected mass to generate a mass delta; and performing a successful formula call on the mass delta.

17. The method of claim 16, further comprising: identifying a second mass in the second dataset that matches the mass delta.

18. The method of claim 17, wherein the mass delta is below 500 Da.

19. The method of claim 17, wherein said matching masses in the second dataset with the selected mass further comprises one or a combination of: identifying a mass in the second dataset that differs from the first or second mass by the theoretical mass of one or more monomer units; identifying a mass in the second dataset that differs from the first or second mass by the theoretical mass one or more monomer units and a biopolymer modification; and identifying a mass in the second dataset that differs from the first or second mass by a theoretical series offset mass.

20. The method of claim 19, wherein said identifying a mass in the second dataset that differs from the first or second mass by the theoretical mass of one or more monomer units comprises:
    generating a resultant mass by adding or subtracting the sum of the theoretical masses of one or more monomer units to or from the first or second mass; and
    identifying a third mass in the second dataset that matches the resultant mass.

21. The method of claim 19, wherein said identifying a mass in the second dataset that differs from the first or second mass by the theoretical mass of one or more monomer units comprises:

generating a mass delta by subtracting a mass in the second dataset from the first or second mass; and performing a successful formula on the mass delta.

22. The method of claim 21, wherein the mass delta is below 500 Da.

23. The method of claim 19, wherein said identifying a mass in the second dataset that differs from the first or second mass by the theoretical mass of one or more monomer units and a biopolymer modification comprises:

generating a first mass delta by subtracting a mass in the second dataset from the first or second mass;

subtracting the theoretical mass of a biopolymer modification from the first mass delta to produce a second mass delta; and performing a successful formula call on the second mass delta.

24. The method of claim 19, wherein said identifying a mass in the second dataset that differs from the first or second mass by a theoretical series offset mass comprises:

generating a resultant mass by adding or subtracting a theoretical series offset mass to or from the first or second mass; and identifying a third mass in the second dataset that matches the resultant mass.

25. The method of claim 1, wherein said comparing the matched masses to determine a monomer sequence for the biopolymer with the selected mass comprises:

grouping the matched masses according to the series type of their corresponding fragments;

calculating mass deltas between pairs of matched masses that correspond to fragments at adjacent positions in a represented series;

performing a formula call on the mass deltas;

assigning monomers associated with the mass deltas based on the formula call; and determining a monomer sequence for the biopolymer with the selected mass based on said assigning.

26. The method of claim 25, further comprising:

calculating mass deltas between pairs of matched masses that correspond to fragments at non-adjacent positions in a represented series;

performing a formula call on the mass deltas; and assigning combinations of monomers associated with the mass deltas based on the formula call.

27. The method of claim 25, further comprising:

calculating mass deltas between pairs of matched masses that correspond to fragments at adjacent positions on different represented series;

performing a formula call on the mass deltas; and assigning monomers associated with the mass deltas based on the formula call.

28. The method of claim 25, further comprising:

calculating mass deltas between pairs of matched masses that correspond to fragments at non-adjacent positions on different represented series;

performing a formula call on the mass deltas; and assigning combinations of monomers associated with the mass deltas based on the formula call.

29. The method of claim 25, wherein the monomer sequence includes a single possible monomer at each position in the sequence.

30. The method of claim 25, wherein the monomer sequence includes more than one possible monomer at a position in the sequence.

31. The method of claim 25, wherein the monomer sequence includes an unknown monomer at a position in the sequence.

32. The method of claim 25, wherein the monomer sequence includes a biopolymer modification at a position in the sequence.

33. The method of claim 1, wherein the biopolymer with the selected mass is a polypeptide and the monomer sequence is an amino acid sequence.

34. The method of claim 1, wherein the biopolymer with the selected mass is a polynucleotide and the monomer sequence is a nucleotide sequence.

35. The method of claim 1, wherein the biopolymer with the selected mass is a polysaccharide and the monomer sequence is a sugar sequence.

36. The method of claim 1, wherein the polysaccharide is linear.

37. The method of claim 1, wherein the polysaccharide is branched.

38. The method of claim 1, wherein:

the sample includes a plurality of biopolymers;

the first dataset includes measured masses of the plurality of biopolymers; and the second dataset includes measured masses of a collection of fragments of the plurality of biopolymers.

39. A computer program product for identifying a biopolymer in a sample that includes one or more biopolymers, comprising a non-transitory computer readable medium configured with a set of machine executable instructions, the instructions comprising:

instructions for selecting a mass from a first dataset, wherein said first dataset includes measured masses of the one or more biopolymers;

instructions for matching masses in a second dataset with the selected mass, wherein said second dataset includes measured masses of a collection of fragments of the one or more biopolymers, and wherein the matched masses represent fragments of the biopolymer with the selected mass; and instructions for comparing the matched masses to determine a monomer sequence for the biopolymer with the selected mass.

40. The computer program product of claim 39, further comprising:

instructions for removing masses from the first dataset that are also present in the second dataset before selecting a mass from the first dataset.

41. The computer program product of claim 39, further comprising:

instructions for removing masses from the second dataset that are also present in the first dataset before selecting a mass from the first dataset.

42. The computer program product of claim 39, wherein said instructions for matching masses in the second dataset with the selected mass comprise:

instructions for subtracting a first mass from the selected mass to produce a mass delta; and instructions for identifying a second mass in the second dataset that matches the mass delta.

43. The computer program product of claim 42, further comprising:

instructions for performing a formula call on the first or second mass.

44. The computer program product of claim 43, wherein said instructions for performing a formula call on the first or second mass are limited to masses below 500 Da.

45. The computer program product of claim 42, further comprising one or a combination of:
   instructions for identifying a mass in the second dataset that differs from the first or second mass by the theoretical mass of one or more monomer units;
   instructions for identifying a mass in the second dataset that differs from the first or second mass by the theoretical mass of one or more monomer units and a biopolymer modification; and
   instructions for identifying a mass in the second dataset that differs from the first or second mass by a theoretical series offset mass.

46. The computer program product of claim 39, wherein said instructions for matching masses in the second dataset with the selected mass comprise:
   instructions for subtracting a first mass in the second dataset from the selected mass to generate a mass delta; and
   instructions for performing a formula call on the mass delta.

47. The computer program product of claim 46, further comprising:
   instructions for identifying a second mass in the second dataset that matches the mass delta.

48. The computer program product of claim 47, wherein said instructions for performing a formula call on the mass delta are limited to mass deltas below 500 Da.

49. The computer program product of claim 47, further comprising one or a combination of:
   instructions for identifying a mass in the second dataset that differs from the first or second mass by the theoretical mass of one or more monomer units;
   instructions for identifying a mass in the second dataset that differs from the first or second mass by the theoretical mass of one or more monomer, units and a biopolymer modification; and
   instructions for identifying a mass in the second dataset that differs from the first or second mass by a theoretical series offset mass.

50. The computer program product of claim 49, wherein said instructions for identifying a mass in the second dataset that differs from the first or second mass by the theoretical mass of one or more monomer units comprise:
   instructions for generating a resultant mass by adding or subtracting the sum of the theoretical masses of one or more possible monomer units to or from the first or second mass; and
   instructions for identifying a third mass in the second dataset that matches the resultant mass.

51. The computer program product of claim 49, wherein said instructions for identifying a mass in the second dataset that differs from the first or second mass by the theoretical mass of one or more monomer units comprise:
   instructions for generating a mass delta by subtracting a mass in the second dataset from the first or second mass; and
   instructions for performing a formula call on the mass delta.

52. The computer program product of claim 51, wherein said instructions for performing a formula call on the mass delta are limited to mass deltas below 500 Da.

53. The computer program product of claim 49, wherein said instructions for identifying a mass in the second dataset that differs from the first or second mass by the theoretical mass of one or more monomer units and a biopolymer modification comprise:
   instructions for generating a first mass delta by subtracting a mass in the second dataset from the first or second mass;
   instructions for subtracting the theoretical mass of a possible biopolymer modification from the first mass delta to produce a second mass delta; and
   instructions for performing a formula call on the second mass delta.

54. The computer program product of claim 49, wherein said instructions for identifying a mass in the second dataset that differs from the first or second mass by a theoretical series offset mass comprise:
   instructions for generating a resultant mass by adding or subtracting a theoretical series offset mass to or from the first or second mass; and
   instructions for identifying a third mass in the second dataset that matches the resultant mass.

55. The computer program product of claim 39, wherein said instructions for comparing the matched masses to determine a monomer sequence for the biopolymer with the selected mass comprise:
   instructions for grouping the matched masses according to the series type of their corresponding fragments;
   instructions for calculating mass deltas between pairs of matched masses that correspond to fragments at adjacent positions in a represented series;
   instructions for performing a formula call on the mass deltas; instructions for assigning monomers associated with the mass deltas based on the formula call; and
   instructions for determining a monomer sequence for the biopolymer with the selected mass based on said assigning.

56. The computer program product of claim 55, further comprising:
   instructions for calculating mass deltas between pairs of matched masses that correspond to fragments at non-adjacent positions in a represented series;
   instructions for performing a formula call on the mass deltas; and instructions for assigning combinations of monomers associated with the mass deltas based on the formula call.

57. The computer program product of claim 55, further comprising:
   instructions for calculating mass deltas between pairs of matched masses that correspond to fragments at adjacent positions on different represented series;
   instructions for performing a formula call on the mass deltas; and
   instructions for assigning monomers associated with the mass deltas based on the formula call.

58. The computer program product of claim 55, further comprising:
   instructions for calculating mass deltas between pairs of matched masses that correspond to fragments at non-adjacent positions on different represented series;
   instructions for performing a formula call on the mass deltas; and instructions for assigning combinations of monomers associated with the mass deltas based on the formula call.

59. The computer program product of claim 39, wherein the biopolymer with the selected mass is a polypeptide and the monomer sequence is an amino acid sequence.

60. The computer program product of claim 39, wherein the biopolymer with the selected mass is a polynucleotide and the monomer sequence is a nucleotide sequence.

61. The computer program product of claim 39, wherein the biopolymer with the selected mass is a polysaccharide and the monomer sequence is a sugar sequence.

62. The computer program product of claim 39, wherein the polysaccharide is linear.

63. The computer program product of claim 39, wherein the polysaccharide is branched.

64. The computer program product of claim 39, wherein:
the sample includes a plurality of biopolymers;
the first dataset includes measured masses of the plurality of biopolymers; and the second dataset includes measured masses of a collection of fragments of the plurality of biopolymers.

* * * * *

UNITED STATES PATENT AND TRADEMARK OFFICE
CERTIFICATE OF CORRECTION

PATENT NO. : 8,507,285 B2  
APPLICATION NO. : 10/388088  
DATED : August 13, 2013  
INVENTOR(S) : Dean R. Thompson et al.

Page 1 of 1

It is certified that error appears in the above-identified patent and that said Letters Patent is hereby corrected as shown below:

On Title Page 2, in column 2, Item (56), under "Other Publications", line 1, delete "Multipexed" and insert -- Multiplexed --, therefor.

In the Claims

In column 24, line 8, in claim 11, delete "rust" and insert -- first --, therefor.

In column 24, line 14, in claim 12, after "mass" insert -- of --.

In column 24, line 51, in claim 19, after "mass" insert -- of --.

In column 27, line 36, in claim 49, delete "monomer," and insert -- monomer --, therefor.

Signed and Sealed this  
Thirteenth Day of May, 2014

Michelle K. Lee  
*Deputy Director of the United States Patent and Trademark Office*